US009038199B2

(12) United States Patent
Becker et al.

(10) Patent No.: US 9,038,199 B2
(45) Date of Patent: May 26, 2015

(54) WELDING HELMET POSITIVE AIR PRESSURING SYSTEM AND METHOD

(75) Inventors: William Joshua Becker, Manitowoc, WI (US); Kenneth S. Dobson, Northville, MI (US); Kui-Chiu Kwok, Gurnee, IL (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 1517 days.

(21) Appl. No.: 12/391,629

(22) Filed: Feb. 24, 2009

(65) Prior Publication Data
US 2009/0210989 A1    Aug. 27, 2009

Related U.S. Application Data

(60) Provisional application No. 61/031,130, filed on Feb. 25, 2008.

(51) Int. Cl.
*A61F 9/06* (2006.01)
(52) U.S. Cl.
CPC ..................... *A61F 9/068* (2013.01)
(58) Field of Classification Search
USPC ............ 2/8.6, 171.3, 209.13, 7, 8.1, 8.2, 422, 2/436, 905, 906; 128/863, 201.22
See application file for complete search history.

(56) References Cited

U.S. PATENT DOCUMENTS

| 2,402,820 | A | * | 6/1946 | Kitchen ................... 128/205.25 |
| 3,649,964 | A | * | 3/1972 | Schoelz et al. ........... 128/205.25 |
| 3,657,740 | A | * | 4/1972 | Cialone .................... 128/205.25 |
| 5,878,742 | A | * | 3/1999 | Figueredo et al. ....... 128/201.24 |
| 7,114,194 | B2 | * | 10/2006 | English .......................... 2/171.3 |
| 7,178,932 | B1 | * | 2/2007 | Buckman ..................... 362/105 |
| 7,534,005 | B1 | | 5/2009 | Buckman |

* cited by examiner

*Primary Examiner* — Andrew W Collins
(74) *Attorney, Agent, or Firm* — Fletcher Yoder P.C.

(57) ABSTRACT

A method and system for controlling ventilation in a welding helmet is provided. The invention may be adapted to a wide variety of system types, and may reduce or eliminate the need for a shroud or barrier around the head and neck of the welder, of the type used in PAPR systems. The airflow system includes forward and rearward air streams, directed onto the face of the welder, onto the top of the head of the welder, and toward the back of the head of the welder. The air streams help to cool the welder, provide a fresh source of air for breathing, and create a positive pressure system that reduces or excludes entrainment of contaminated external air into the forwardly directed air flow. Certain embodiments may include streams that are filtered, split or redirected via deflectors and conduits to achieve the aforementioned goals.

6 Claims, 4 Drawing Sheets

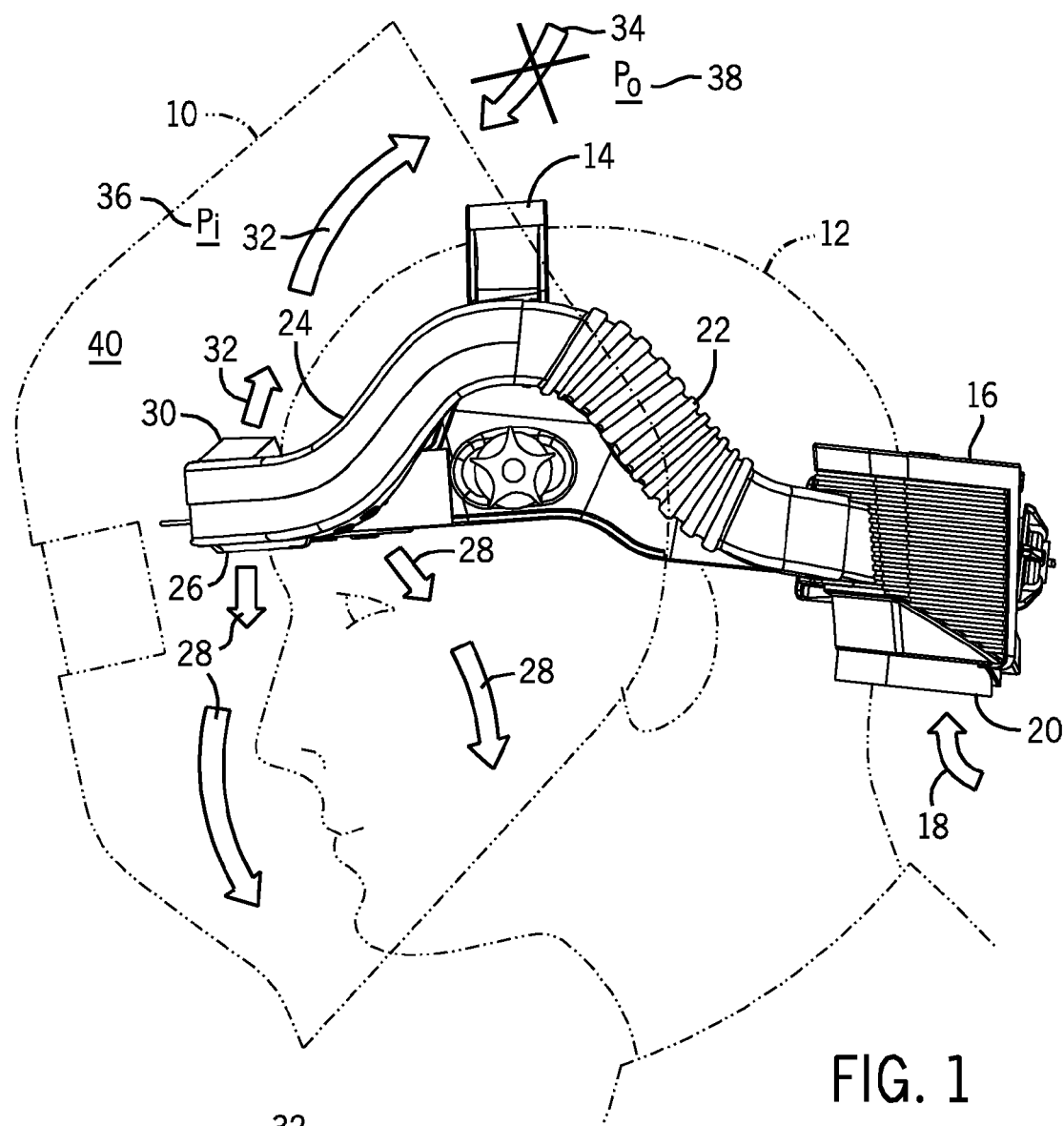
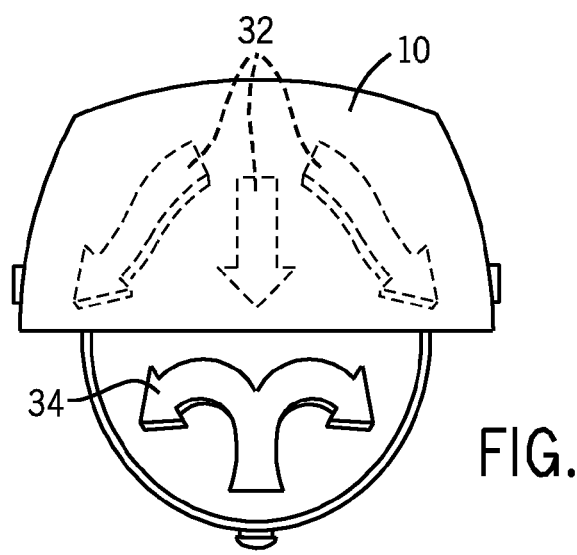
FIG. 1
FIG. 2

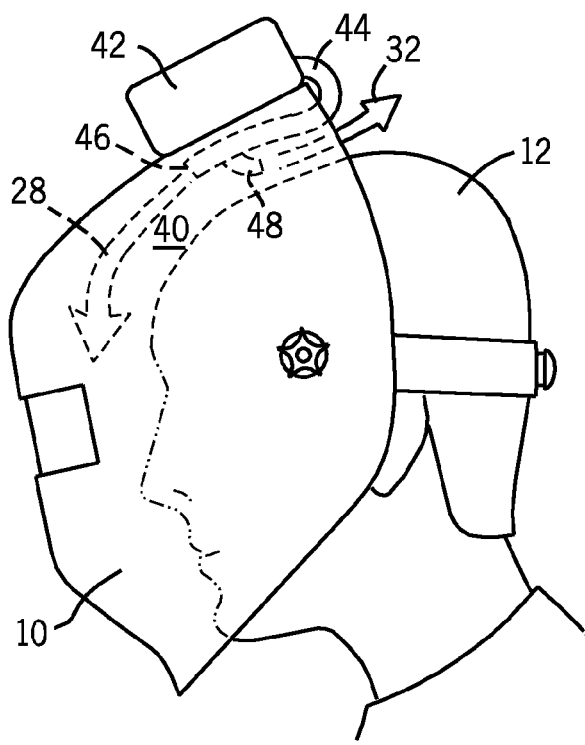
FIG. 3
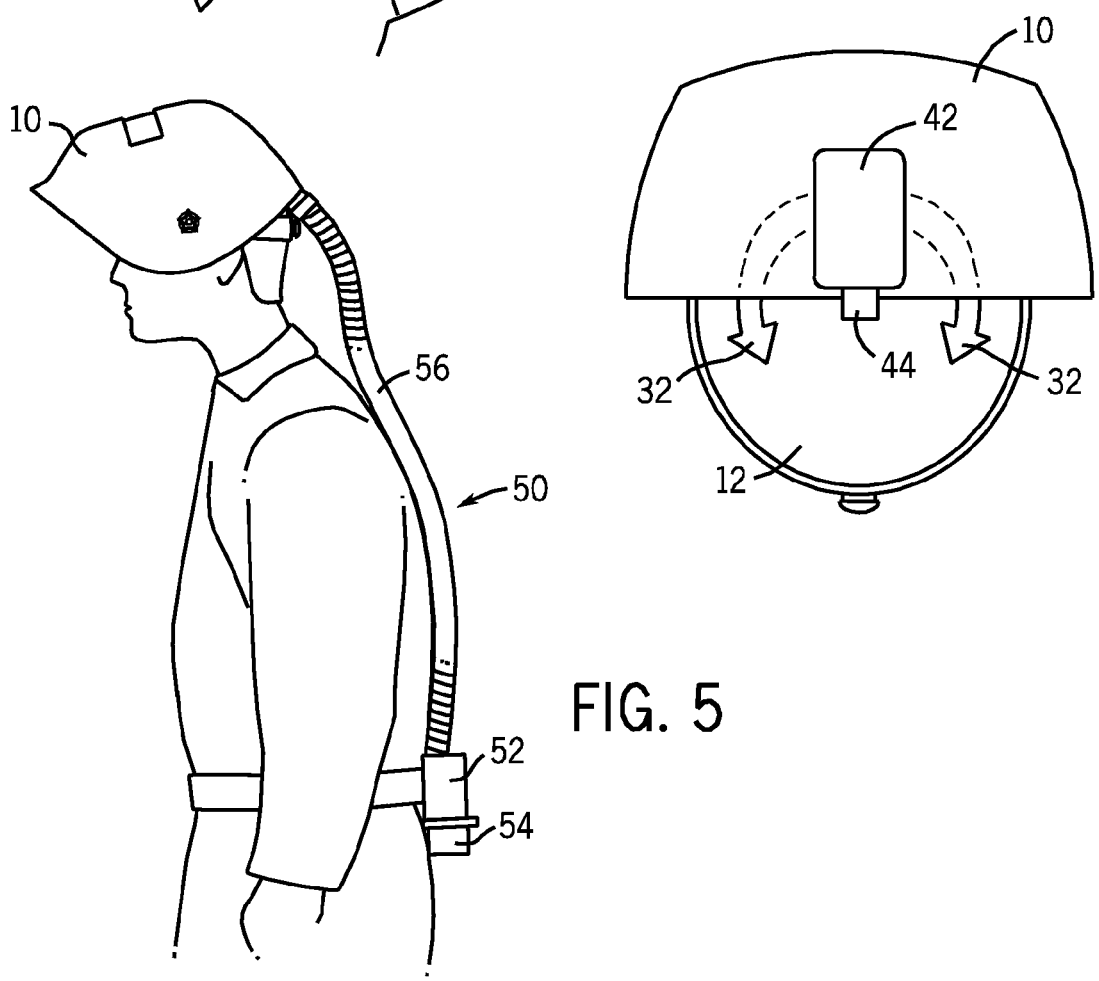
FIG. 4
FIG. 5

WELDING HELMET POSITIVE AIR PRESSURING SYSTEM AND METHOD

CROSS REFERENCE TO RELATED APPLICATIONS

This application is a Non-provisional Patent Application of U.S. Provisional Patent Application No. 61/031,130, entitled "Air Quality Neutralization Means In A Helmet Airflow System", filed Feb. 25, 2008, which is herein incorporated by reference.

BACKGROUND

The invention relates generally to cooling and filtering systems for welding helmets.

The invention relates generally to welding helmets, and more particularly to arrangements for controlling the influx of air into a welding helmet.

Welding can be a heat intensive process, especially during the summer months in outdoor locations or in plants without air conditioning or good air circulation. Furthermore, welding environments contribute fumes and particulates to the locations in which welding is performed. While some industrial standards exist that require powered air purifying respirator (PAPR) systems, such standards may not apply to all situations in which improved air circulation may be desirable for operator comfort, particularly over extended periods of work. Moreover, when not required, PAPR systems represent a relatively costly approach to ventilation and cooling. Further, PAPR systems generally include a shroud or blanket arrangement that covers the head and neck of the welder, which can be cumbersome to don, doff and wear.

Many welding environments may remain quite uncomfortable, particularly over extended periods of welding work, due to lack of sufficient cooling or ventilating air flow, reducing worker productivity and satisfaction. Welders may, for example, take more frequent breaks than would be otherwise needed to provide rest. Where cost permits, welders in less intense environments may opt for a PAPR system, but many are discouraged by the high level of discomfort associated with these bulky systems, as well as the associated costs. Thus, for environments in which PAPR systems are not required, there exists a need for effective systems that controls air flow in a welding helmet, and, particularly, that reduce the entrainment of unfiltered outside air during use.

BRIEF DESCRIPTION

The present invention provides a novel welding helmet ventilation system designed to respond to such needs. The invention may be adapted to a wide variety of system types, and may reduce or eliminate the need for a shroud or barrier around the head and neck of the welder, of the type used in PAPR systems. In particular, the invention provides a method and system for controlling airflow in a welding helmet. The airflow system provides a forward air stream directed onto the face of the welder and a rearward air stream directed onto the top of the head of the welder and/or toward the back of the head of the welder for the dual purposes of cooling the welder and creating a positive pressure system that excludes external airflow. Certain embodiments may include streams that are filtered, split or redirected via deflectors and conduits to achieve the aforementioned goals.

DRAWINGS

These and other features, aspects, and advantages of the present invention will become better understood when the following detailed description is read with reference to the accompanying drawings in which like characters represent like parts throughout the drawings, wherein:

FIG. 1 is a side view of a welder wearing an exemplary welding helmet with an integrated air flow system in accordance with aspects of the present invention;

FIG. 2 is a top plan view of the air flow in the system of FIG. 1;

FIG. 3 is a side view of a welder wearing a welding helmet coupled to an external blower mounted to the top of the helmet and also incorporating air flow in accordance with the invention;

FIG. 4 is a top plan view of the air flow in the system of FIG. 3;

FIG. 5 is a side view of a welder wearing a ventilation system mounted to the back of the welder and also incorporating air flow in accordance with the invention;

DETAILED DESCRIPTION

Figure 6:
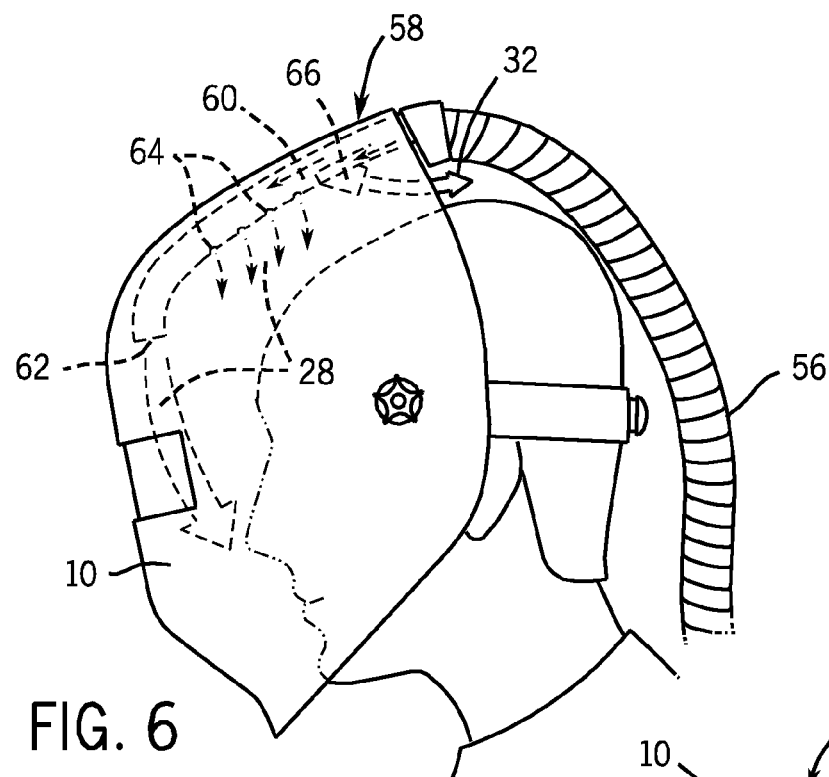
FIG. 6 is a side view of the head of a welder wearing the ventilation system of FIG. 5.

FIG. 1 illustrates an exemplary welding helmet 10 that incorporates an integrated air flow system in accordance with aspects of the invention. The head of the welder 12 may don headgear 14, which contains straps that provide support and stability for the welding helmet 10. An airflow system 16 may be attached to or integrated into the headgear 14 and may generally follow the circumference of the headgear 14. In certain embodiments, the airflow system may be permanently attached to the headgear. In such an embodiment, the headgear itself may serve as part of the air conduit. However, in other embodiments, the airflow system may be affixed to the headgear using mounting brackets or other attachment methods. By generally following the circumference of the headgear 14, the airflow system 16 may be located close to the user's head to promote stability and balance when worn.

Air 18 may enter the airflow system through an air intake 20 that is located at the rear of the headgear 14. The rear location allows the air 18 to enter the airflow system 16 from an area behind the user 12. The area behind the user 12 may contain a lower amount of welding fumes, particulates, and gases other than the area in front of the user 12 where the welding operation is performed. The air is first at an air intake 20, from which the air may flow through a flexible conduit 22 into a manifold 24. The flexible conduit 22 may include flexible tubing disposed on one side of the user's head, generally along one of the headgear straps. The manifold 24 may direct the air to a lower vent 26 where the air exits the airflow system 16 and is directed transversely toward a user's face and breathing zone, as indicated generally by arrows 28. The air may also be directed transversely through an upper vent 30, as indicated generally by arrows 32. From upper vent 30, the air 32 may flow up and over a user's head generally toward the rear of the airflow system 16. It should be noted that some of the forwardly directed air, part of the rearwardly directed air, or both may be directed to sides of the helmet to prevent entrainment of air from those locations as well. While it may be difficult or impossible to cover all possible entry points, creating a positive internal pressure, and directing air towards the rear and sides together, limits or greatly reduces the tendency to draw unfiltered environmental air into the helmet.

The air from the vents 26 and 30 may function to provide positive pressure and impede air that has not flowed through the airflow system 16 from entering the breathing zone of the welder 40. In general, such positive pressure forms by virtue of the pressure of air exiting the vents 26 and 30 which will be at a somewhat higher pressure than the surrounding air (as required to create the flow within the helmet). The internal pressure, as indicated generally by reference numeral 36, counters the external pressure 38 outside the helmet, prohibiting air 34 from the surrounding environment to enter. In a presently contemplated embodiment, the internal air flow from vents 26 and 30 offers a somewhat positive pressure at most locations where the helmet is open to the surrounding air, including below the user's face, on the sides of the helmet, and in back of the helmet above the rear of the user's head.

FIG. 2 is a top plan view of the rearward flow of air 32 from the vent 30 toward the back of the head of the welder. This airflow 32 creates a positive pressure system that forces external environmental air 34 away from the welding helmet 10, prohibiting entry into the breathing zone of the welder. In other embodiments, a fabric structure may be attached to the welding helmet to create a seal or barrier between the welding helmet 10 and the head and/or neck of the user 12 to impede unfiltered air from entering the breathing zone of the user. However, the pressure difference between air provided by the circulation system and the external air advantageously reduces or eliminates the need for such barriers, which may prove unwieldy or hot for the user. Particularly important is the elimination of inflowing air from the rear and side zones of the helmet that might otherwise occur if a forwardly directed stream of air alone were provided towards the user's face.

FIG. 3 illustrates the head of a welder 12 with a welding helmet outfitted with an external blower 42. In this embodiment, the external blower 42 may be permanently attached to the helmet, or may be temporarily fitted, such as by clips, screw clamps and so forth (not shown). The external blower 42 acts as a source of a filtered air stream through a conduit 44 that loops around the edge of the helmet and directs air into the helmet. This air stream, which is filtered as in the previous embodiment, splits into a forward exhaust 46, which enters the breathing zone of the welder 40, and a rearward exhaust 48, which exits the back of the welding helmet 10. The rearward exhaust 48 may also direct air towards the sides of the helmet, or additional exhausts may be provided for that purpose. As in the previous embodiment, a positive pressure system is created, as shown in the top plan view in FIG. 4. That is, an internal pressure 36 created by the airflow 32 prohibits external air 34, which may be contaminated with particulates and debris, from entering the breathing zone of the welder 40.

FIG. 5 illustrates a further embodiment in which a ventilation system 50 is carried on the back of the welder, which may employ the invented method for airflow control. The general arrangement of the ventilation system may be similar to a PAPR system, but the air flow and pressure relationships may reduce or eliminate the need for physical barriers around the helmet. The embodiment illustrated in FIG. 5 includes a battery and blower pack 52 that produces a flow of air that is directed into the helmet. A filter 54 filters air from the back of the welder, which is typically cleaner than environmental air closer to the welding location, and feeds the filtered air into the battery and blower pack 52. The battery and blower pack 52 is connected to a conduit 56, which feeds filtered air into the welding helmet 10.

Figure 7:
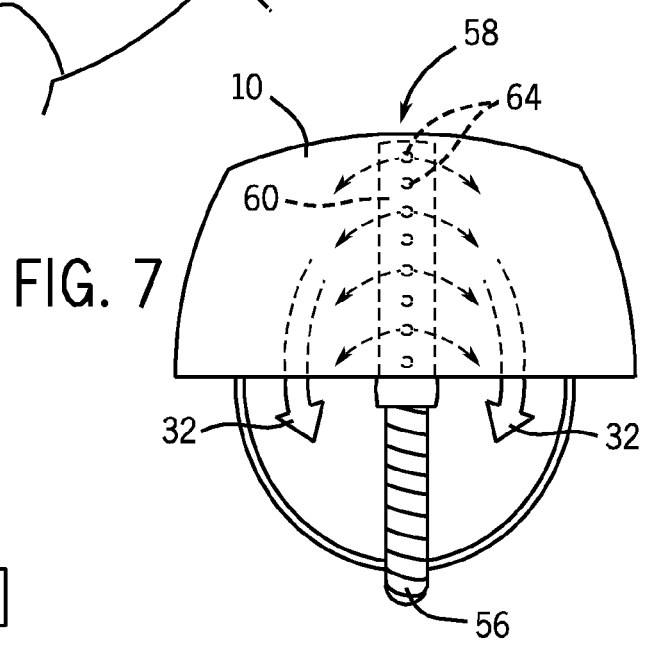
FIG. 7 is a top plan view of the air flow in the ventilation system of FIG. 5.
Figure 8:
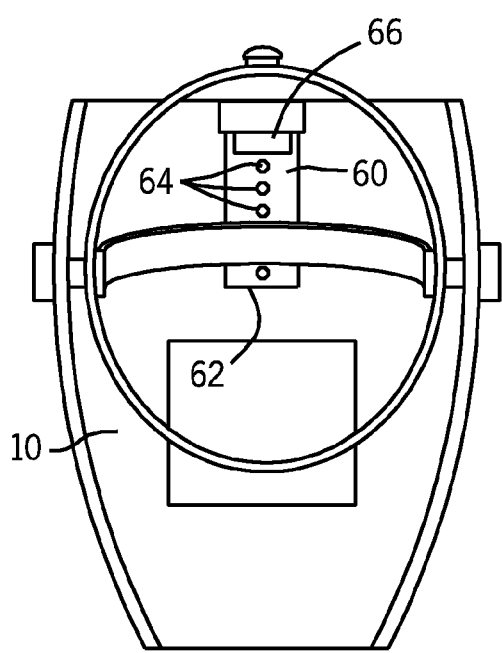
FIG. 8 is a top plan view of the inside of the welding helmet of FIG. 6.

FIG. 6 illustrates this system in a side view on the head of the welder 12 with the welding helmet 10 in a welding position. An air distribution system 58 passes air through an upper conduit 60 to release both forward exhaust 62, which enters the breathing zone of the welder 40, and a top exhaust through apertures 64 in the upper conduit 60, which provides air flow to the top portion of the head. The airflow path feeding from the conduit 56 to the air distribution system can be seen in FIG. 7 in the top plan view of the head of the welder. The air distribution system provides air flow to the breathing zone of the welder, the top of the head of the welder, and the rear of the welding helmet to both cool the welder and prevent entrainment of outside air. That is, as in the previous embodiments, a positive pressure system is created by the rear exhaust 66, which maintains the internal pressure 36 at a level greater than the external pressure 38, eliminating contamination of the air in the breathing zone of the user that might otherwise occur. The upper conduit 60, with its forward exhaust 62 and apertures 64, as well as the rear exhaust 66 are also shown in the rear view of the helmet illustrated in FIG. 8.

Figure 9:
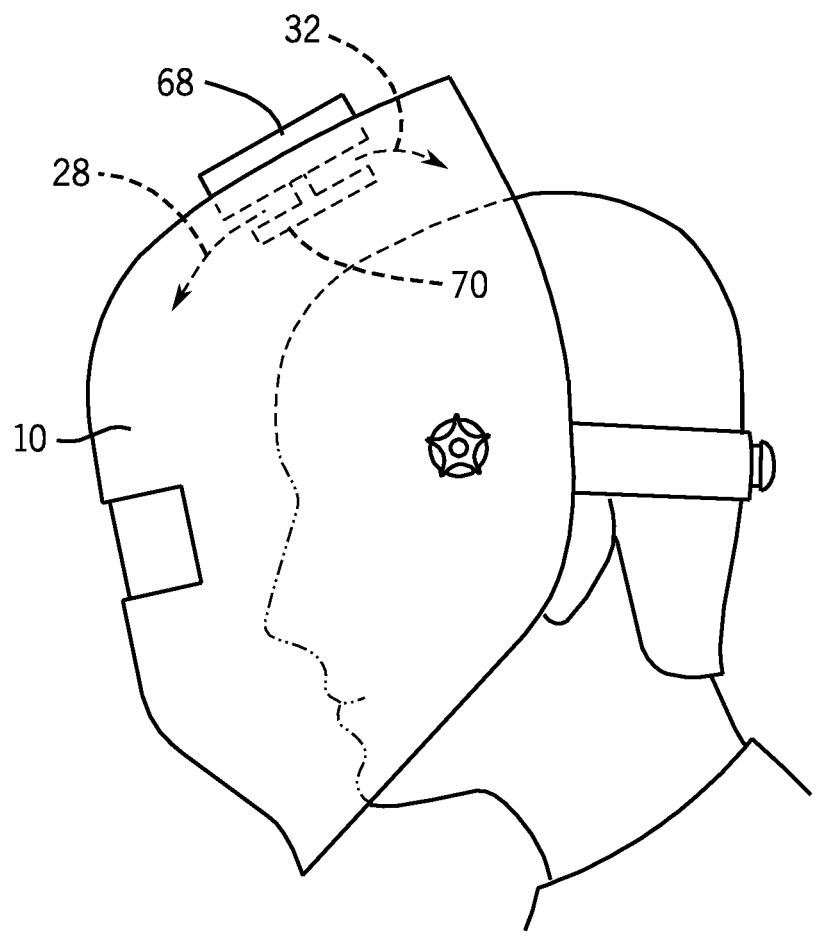
FIG. 9 is a side view of a welder wearing a welding helmet with an integrated blower and also incorporating air flow in accordance with the invention.

As a further alternative, the helmet may be provided with an integrated ventilation system as generally illustrated in FIG. 9. In this embodiment, the ventilation system 68 includes an element (that may extend from the helmet or be generally flush with the outer shell) that draws in environmental air, filters the air and blows the air through a structure within the helmet. This type of arrangement may be provided with the helmet as an original integrated component, or may be retrofitted to the helmet. An air distribution structure 70 directs air streams 28 and 32 towards the front of the helmet (towards the face of the welder), and towards the rear and/or sides of the helmet. The positive pressure offered by the rearwardly directed air, as in the previous embodiments, reduces the tendency of the integrated ventilation system 68 to draw in unwanted environmental air.

While only certain features of the invention have been illustrated and described herein, many modifications and changes will occur to those skilled in the art. It is, therefore, to be understood that the appended claims are intended to cover all such modifications and changes as fall within the true spirit of the invention. For example, the particular arrangement of exhausts, vents, air flow channels and conduits may be altered from those illustrated to provide various air flow patterns and pressure zones. In general, however, such alterations will offer cleaner air around the face of the user, while creating air flow and pressure areas that preclude the entrainment of contaminated air into the forwardly directed air.

The invention claimed is:

1. A method for controlling air flow in a welding helmet comprising:
    directing a forward air stream within the helmet forwardly through a conduit extending to the face of a welder;
    directing a rearward air stream within the helmet rearwardly with a deflector disposed on the conduit to reduce or prevent entrainment of air from a rear region of the helmet into the forward air stream; and
    wherein the forward air stream is directed forwardly onto a generally top portion of the head of the welder.

2. The method of claim 1, wherein the conduit has one or more apertures for passing the forward air stream.

3. The method of claim 1, wherein the forward air stream is directed generally onto the face of the welder.

4. The method of claim 1, wherein the deflector has one or more apertures for passing the rearward air stream.

5. The method of claim 1, wherein the forward and rearward air streams are split from a common feeder air stream.

6. The method of claim 1, comprising directing a sideward air stream that reduces or prevents entrainment of air from a side region of the helmet.

* * * * *